United States Patent [19]

Niwa et al.

[11] Patent Number: 4,780,824
[45] Date of Patent: Oct. 25, 1988

[54] AUTOMATIC BLOOD PRESSURE MONITORING SYSTEM

[75] Inventors: Minoru Niwa, Nagoya; Hifumi Yokoe, Kasugai, both of Japan

[73] Assignee: Nippon Colin Co., Ltd., Aichi, Japan

[21] Appl. No.: 947,829

[22] Filed: Dec. 29, 1986

[30] Foreign Application Priority Data

Dec. 27, 1985 [JP] Japan .................................. 60-299572

[51] Int. Cl.$^4$ .............................................. G06G 7/60
[52] U.S. Cl. ............................... 364/413.07; 128/667; 128/671
[58] Field of Search ........................ 128/666, 667, 671; 364/416, 417

[56] References Cited

U.S. PATENT DOCUMENTS

| | | |
|---|---|---|
| 3,412,729 | 11/1968 | Smith, Jr. . |
| 3,998,550 | 12/1976 | Konishi et al. . |
| 4,013,067 | 3/1977 | Kresse .............................. 128/666 |
| 4,090,505 | 5/1978 | Mortara ............................. 128/666 |
| 4,202,339 | 5/1980 | Wirtzfeld et al. . |
| 4,259,963 | 4/1981 | Huch .................................. 128/635 |
| 4,566,463 | 1/1986 | Taniguchi ......................... 128/682 |

OTHER PUBLICATIONS

"Continuous, Non-Invasive Measurements of Arterial Blood Oxygen Levels", Merrick et al., Hewlett-Packard Journal, vol. 28, No. 2, Oct. 1976, pp. 2–9.

Primary Examiner—Jerry Smith
Assistant Examiner—Steven G. Kibby
Attorney, Agent, or Firm—Parkhurst, Oliff & Berridge

[57] ABSTRACT

An automatic blood pressure monitoring system includes a device which detects the degree of saturation of oxygen in the blood at a peripheral part of the body. The detecting device generates a signal if the degree of saturation is detected to be abnormal. A control device operates a blood pressure measuring device in response to the signal indicating abnormal oxygen saturation. In a second embodiment, a trigger device periodically generates a signal to operate the blood pressure measuring device. When an abnormal oxygen saturation is detected, a signal operates the blood pressure measuring device and the triggering interval is shortened.

9 Claims, 4 Drawing Sheets

AUTOMATIC BLOOD PRESSURE MONITORING SYSTEM

BACKGROUND OF THE INVENTION

1. Field of the Art

The present invention relates in general to an automatic blood pressure monitoring system, and in particular to such a system which automatically obtains a measure of an blood pressure upon detection of abnormality in the degree of saturation of oxygen in the blood of a subject being monitored.

2. Related Art Statement

There is known in the art an automatic blood pressure monitoring system having an inflatable cuff which is wound around a part of a subject or living body to be monitored, so as to oppress the part, and also having determining means which determines a measure of blood pressure based on fluctuations of pulse waves that are caused in association with variation in the pressure in the inflatable cuff. In order to capture such fluctuations of the pulse waves, a variety of indications or signs are utilized such as: appearance and disappearance of Korotkov's sounds which are heard at the part of the subject, while the cuff is deflated; change in the magnitude of oscillations of the pressure in the cuff which are caused in synchronous relationship with heartbeats of the subject; or change in the magnitude of pulsations on the surface of the wall of an artery that are detected by means of ultrasonic wave. A conventional automatic monitoring system of such a type is adapted to obtain blood pressure measurements, according to starting signals supplied periodically, for the purpose of, for example, monitoring a patient (subject) during or after a surgical operation procedure.

3. Problem Solved by the Invention

In the above-identified type of automatic monitoring system, a measure of blood pressure is not necessarily obtained at the time the subject being monitored is brought into an abnormal state with respect to the degree of saturation of oxygen in the blood, due to shock or cyanosis, since such measurement is conducted at regular intervals of time. That is, the conventional system is not able to obtain a measure of blood pressure at the time the measure is clinically needed for monitoring the condition of the subject. An automatic monitoring system for monitoring a subject's blood pressure during or after a surgical operation, is required from the clinical viewpoint to be able to obtain a measure of blood pressure at the very time the subject is brought into an abnormal state.

Meanwhile, it is possible to obtain a measure of blood pressure at the time approximate to the time of occurrence of an abnormality of the subject, by means of using starting signals generated at shortened intervals and performing the operation of obtaining blood pressure measurements at shortened cycles. This method is, however, disadvantageous since the subject suffers unnecessary oppression by the inflatable cuff that is repeatedly inflated and deflated, and may have congestion at the part around which the cuff is wound.

SUMMARY OF THE INVENTION

It is therefore an object of the present invention to provide an improved automatic blood pressure monitoring system.

It is another object of the invention to provide an automatic blood pressure monitoring system which can obtain a measure of blood pressure of a subject at the time the subject is brought into an abnormal state with respect to the degree of saturation of oxygen in blood.

According to the present invention, there is provided an automatic blood pressure monitoring system for automatically obtaining blood pressure measurements, which includes: (a) determining means for determining a measure of blood pressure of a living body; (b) detecting means for detecting a degree of saturation of oxygen in blood which flows in a peripheral part of the living body, the detecting means generating a signal representative of abnormality an if the degree of saturation of oxygen is found abnormal; and (c) control means responsive to the signal supplied from the detecting means, to start the determining means to obtain the measure of blood pressure of the living body.

In the automatic blood pressure monitoring system constructed as described above, blood pressure measurement is timely conducted, for example, at the time a patient being monitored becomes worse with respect to the degree of saturation of oxygen in the blood during or after a surgical procedure. This is very advantageous as viewed from the clinical standpoint, because change of the condition of the patient can be evaluated at once. The instant monitoring system provides another advantage of obtaining necessary measurements only, as opposed to the conventional system of the type in which blood pressure measurements are obtained periodically, i.e., at intervals. Thus, the patient or subject being monitored is relieved of unnecessary oppression applied to the body and/or of congestion due to such unnecessary oppression.

The detecting means of the instant blood pressure monitoring system an abnormality in the degree of saturation of oxygen in the blood, at a pheripheral part of the subject. In addition, a change or abnormality in the condition of the circulatory system initially appears at the pheripheral part of the subject. Therefore, the instant monitoring system can detect a shock condition of the subject immediately and obtain a measure of blood pressure at once.

In a preferred embodiment of the above-mentioned blood pressure monitoring system, the detecting means includes an air bag for oppressing the peripheral part of the living body so as to remove the blood out of veins and arteries of the peripheral part. The detecting means also includes a lamp for emitting light toward the pheripheral part of the living body. The lamp emits light in both conditions: where the peripheral part is oppressed by the air bag and where the peripheral part is not oppressed by the air bag, i.e., in its normal state. The light emitted by the lamp is of a nature to be transmitted through the peripheral part of the living body. The light having been passed through the peripheral part of the living body is selectively received by first and second sensor means, in both of the above-indicated conditions. The first sensor means selectively receives first light out of the transmitted light. The first light received by the first sensor means is of a nature in which the amount thereof is varied in association with the volume of blood at the peripheral part and the quantity of tissue at the peripheral part but by no means affected by the degree of saturation of oxygen in the blood at the peripheral part. The first sensor means generates first signal corresponding to the amount of the first light received, in the above both cases. In the meanwhile, the second sensor means selectively receives second light out of the light having been passed through the peripheral part, in the both cases. The second light is of a nature in which the amount thereof is varied in association with the volume of blood at the periphral part, the quantity of tissue at the peripheral part and the degree of saturation of oxygen in the blood. The second sensor means generates second signal corresponding to the amount of the second light received, in the both cases.

In a preferred form of the above-indicated embodiment of the invention, the detecting means further includes calculator means for receiving the first signal from the first sensor means and the second signal from the second sensor means, in the above-mentioned both cases. The calculator means determines a degree of saturation of oxygen in the blood of the peripheral part of the living body, based on the first and second signals received in the both cases, and generates detection signal representative of the degree determined. The detecting means further includes storing means for storing a reference degree of saturation and generating reference signal representative of the reference degree stored. The detecting means also includes abnormality discriminator means for receiving the detection and reference signals, checking if the degree determined by the calculator means is abnormal over the reference degree stored by the storing means, and generating to the control means abnormality signal representative of abnormality if the degree determined by the calculator means is found abnormal.

According to another aspect of the present invention, there is provided an automatic blood pressure monitoring system for automatically obtaining blood pressure measurements. This monitoring system includes; (a) determining means for determining a measure of blood pressure of a living body; (b) detecting means for detecting a degree of saturation of oxygen in blood which flows in a peripheral part of the living body, the detecting means generating signal representative of abnormality if the degree of saturation of oxygen is found abnormal; and (c) trigger means for generating first signal at intervals to periodically start the determining means so as to determine the measure of blood pressure of the living body. The trigger means is responsive to the signal supplied from the detecting means, to generate second signal at intervals shorter than the intervals at which to generate the first signal, so as to periodically start the determining means for determining the measure of blood pressure.

The above monitoring system can continuously obtain blood pressure measurements at shortened intervals in the case where the subject being monitored becomes worse with respect to the degree of saturation of oxygen in the blood. This is very advantageous from the clinical standpoint.

BRIEF DESCRIPTION OF THE DRAWING

The above and optional objects, features and advantages of the present invention will be better understood by reading the following detailed description of preferred embodiment of the invention, when considered in connection with the accompanying drawings, in which.

DETAILED DESCRIPTION OF THE PREFERRED EMBODIMENT

There will be described in detail the preferred embodiment of the present invention, in connection with the accompanying drawings.

Figure 1:
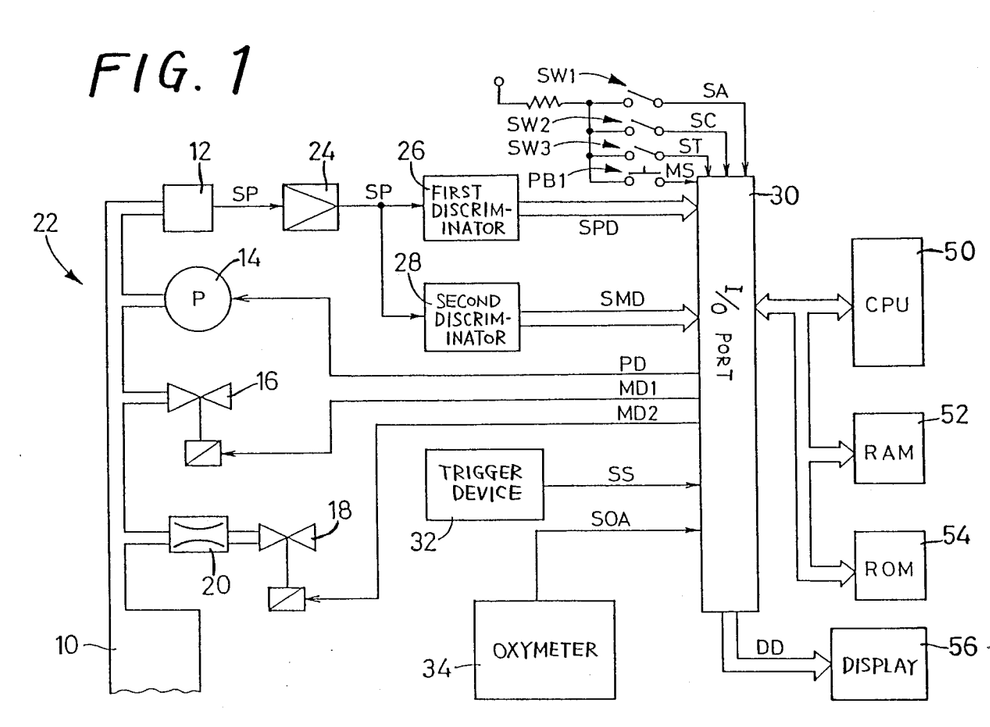
FIG. 1 is a diagrammatical view illustrating one embodiment of an automatic blood pressure monitoring system according to the present invention.

There is diagrammatically shown in FIG. 1 an arrangement of an automatic blood pressure monitoring system in which the so-called "oscillometric method" is employed for obtaining blood pressure measurements. The system embodies the present invention. In this connection, it is noted that the present invention is applicable to other types of automatic blood pressure monitoring systems such as of the type in which blood pressure measurements are obtained by detecting Korotkov's sounds through a microphone, or of the type in which blood pressure measurements are obtained by sensing fluctuations of waves propagated on the surface of the wall of an artery by means of ultrasonic wave.

In FIG. 1, reference numeral 10 designates an inflatable cuff. The inflatable cuff 10 is wound around an arm of a subject or patient, so as to oppress the arm. The inflatable cuff 10 is coupled to a pressure sensor 12, electrically-operated pump 14, and rapid-deflation solenoid valve 16, respectively. The cuff 10 is also coupled to a slow-deflation solenoid valve 18 via a restrictor member 20. The pressure sensor 12 detects a level of pressure in the inflatable cuff 10 and generates signal SP representative of the detected level of the pressure. The electrically-operated pump 14 inflates the inflatable cuff 10 so as to raise the pressure in the cuff 10. The slow-deflation solenoid valve 18 slowly deflates the cuff 10 so as to gradually lower the pressure in the cuff 10, after the cuff 10 has been inflated by the pump 14. While the cuff 10 is slowly deflated by the slow-deflation solenoid valve 18, a measure of blood pressure is obtained from the subject. The rapid-deflation solenoids valve 16 rapidly deflates the cuff 10, after a measure of blood pressure has been obtained. The members 10, 14, 18, 20 cooperate with each other to constitute a cuff device 22 as means for oppressing a part of the subject and gradually removing the oppression from the part.

The signals SP generated by the pressure sensor 12 are supplied, via an amplifier 24, to first discriminator 26 and second discriminator 28, respectively. The first discriminator 26 is equipped with low-pass filter and A/D converter, and filters the signals SP received, so as to remove signals corresponding to pulse waves which are propagated to the cuff 10 in synchronous relationship with heartbeats of the subject. The first discriminator 26 converts the filtered signals SP into digital signals SPD indicative of variation in static pressure in the cuff 10. The signals SPD are then supplied to I/O port 30. On the other hand, the second discriminator 28 is equipped with band-pass filter and A/D converter, and filters the signals SP supplied, so as to collect the signals corresponding to the pulse waves that should have been removed at the first discriminator 26. The second discriminator 28 collects signals corresponding to pulse waves with a frequency ranging from 1.0 to 50 Hz, for example. The filtered signals SP are converted into digital signals SMD, and then supplied to the I/O port 30.

The instant blood pressure monitoring system is provided with various switches; automatic-operation switch SW1, periodical-measuring switch SW2, manual-operation switch SW3, and starting button PB1. The automatic-operation switch SW1 is operated to supply to the I/O port 30 signal SA utilized for placing the instant system in its automatic operation mode. The periodical-measuring switch SW2 is operated to supply to the I/O port 30 signal SC utilized for placing the system in its periodical-measuring mode. The manual-operation switch SW3 is operated to supply to the I/O port 30 signal ST used for placing the system in its manual-operation mode.

The starting button PB1 indicated above is depressed to generate to the I/O port 30 signal MS used for starting the system to obtain a measure of blood pressure of the subject, in the manual-operation mode of the system. In the periodical-measuring mode, a trigger device 32 periodically generates signal SS utilized for starting the system for obtaining a blood pressure measurement. The signal SS is supplied to the I/O port at regular intervals of 1 to 120 minutes.

In the automatic-operation mode, an oxymeter 34 generates to the I/O port 30 signal SOA representative of an abnormal degree of saturation of oxygen in blood which flows in a peripheral part of the subject, so as to start the operation of measurement of blood pressure. The oxymeter 34 serves as detecting means for detecting a degree of saturation of oxygen in the blood of the subject, in the instant automatic blood pressure monitoring system according to the present invention.

Figure 2:
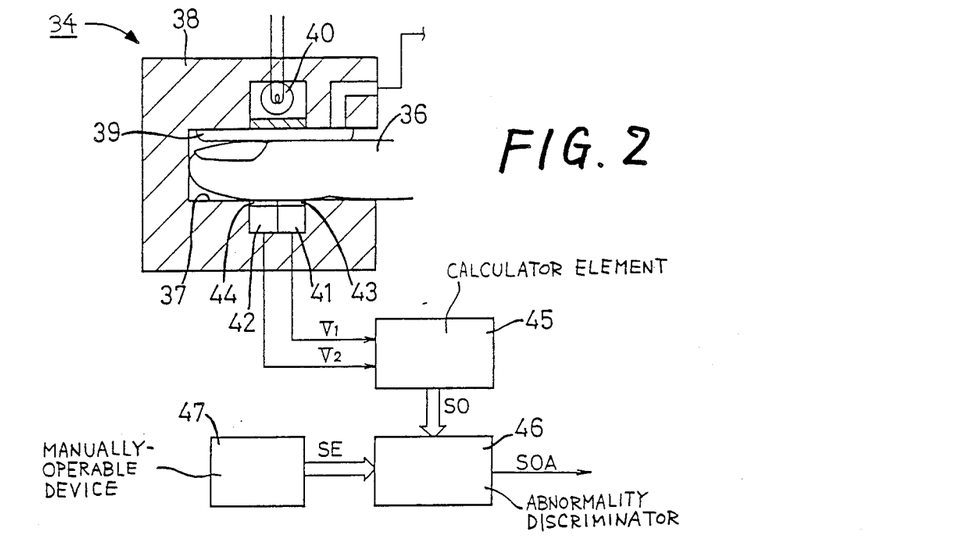
FIG. 2 is a diagrammatical view illustrating an oxymeter of the monitoring system of FIG. 1.

The oxymeter 34 is constructed as illustrated in FIG. 2. The oxymeter 34 includes a block 38 in which a receiver hole 37 is formed. Into the receiver hole 37 is inserted a peripheral part of the subject to be monitored, such as a finger 36. An air bag 39 is disposed on an inner wall of the block 38. Air is supplied to the air bag 39 from an air supply (not shown), as needed, so as to oppress the finger 36. A lamp 40 is embedded in an inner wall of the block 38. Electric power is applied to the lamp 40 from an electric power supply (not shown), so as to light the lamp 40. The lamp 40 emits light which has characteristics of being transmitted through the finger 36. In a wall opposed to the wall in which the lamp 40 is embedded, are embedded a first photosensor 41 and a second photosensor 42. The first photosensor 41 is equipped with a first filter 43 which permits only infrared rays with about 800 m$\mu$ wavelengths to pass therethrough, while the second photosensor 42 is equipped with a second filter 44 which permits only rays with about 600 m$\mu$ wavelengths to pass therethrough. The about 800 m$\mu$ wavelengths light received by the first photosensor 41 is of a nature in which the amount thereof is not affected by the degree of saturation of oxygen in blood within the finger 36, but is varied in association with the volume of blood and quantity of tissue of the finger 36. On the other hand, the about 600 m$\mu$ wavelength light received by the second photosensor 42 is of a nature in which the amount thereof is varied in association with the degree of saturation of oxygen in the blood, the volume of the blood, and the quantity of the tissue of the finger 36. The first and second photosensors 41 and 42, each being a photocell, generates signal V1 and V2, respectively, corresponding to respective electromotive forces v1 and v2 which are caused by the respective kinds of light received.

In general, the degree S of saturation of oxygen in blood is expressed as percentage (%) obtained by dividing the amount of hemoglobin oxide by the total amount of hemoglobin in the blood. The degree S is determined by the following Equation (1):

$$S = K1 + K2 \cdot \frac{\log R2' - \log R2}{\log R1' - \log R1} \qquad (1)$$

where,

R2': amount of light having been passed through finger 36 with the blood removed, corresponding to signal V2 in the case where finger 36 is oppressed by air bag 39;

R2: amount of light having been passed through normal finger 36, corresponding to signal V2 in the case where finger 36 is not oppressed by air bag 39;

R1': amount of light having been passed through finger 36 with the blood removed, corresponding to signal V1 in the case where finger 36 is oppressed by air bag 39;

R1: amount of light having been passed through normal finger 36, corresponding to signal V1 in the case where finger 36 is not oppressed by air bag 39; and K1 and K2: constant, respectively.

Calculator element 45 calculates a degree of saturation of oxygen, as follows. First, the calculator element 45 inflates commands an air supply (not shown) to inflate the air bag 39 to occlude or oppress the finger 36 so as to remove the blood out of the finger 36, i.e., make veins and arteries of the finger 36 vacant, and then deflates the air bag 39 so as to place the finger in its normal state. Thus, the first and second photosensor 41 and 42 generate signal V1 and V2, respectively, in both cases where blood is removed from the finger 36 due to the oppression by the air bag 39 and where the finger 36 is not oppressed, i.e., in its normal state. Based on the signals V1 and V2 received, the calculator element 45 determines a degree S of saturation of oxygen in the blood of the subject being monitored, according to the Equation (1). Subsequently, the element 45 supplies signal SO representative of the thus obtained degree S, to abnormality discriminator 46. In the meantime, the abnomality discriminator 46 receives from a manually-operable device 47 signal SE representative of a reference degree of saturation of oxygen. The discriminator 46 generates signal SOA representative of abnormality of the degree S, if the degree S represented by signal SO received is found to be below the reference degree indicated by signal SE supplied from the device 47.

Referring back to FIG. 1, the above-indicated I/O port 30 is connected by way of data bus line to central processing unit (CPU) 50, random access memory (RAM) 52, and read only memory (ROM) 54, respectively. The CPU 50, RAM 52 and ROM 54 cooperate with each other to constitute computer serving as control means which executes a sequence of steps for starting determining means for determining a measure of blood pressure of the subject. The CPU 50 processes signals received at the I/O port 30 according to the program which is stored in the ROM 54, while utilizing the RAM 52 for the purpose of temporarily storing the signals received. The CPU 50 generates signals PD, MD1 and MD2 to the electrically-operated pump 14, rapid-deflation solenoid valve 16, and slow-deflation solenoid valve 18, respectively, for the purpose of actuating the respective members 14, 16 and 18. The CPU 50 also generates to a display 54 signal DD representative of the measure of blood pressure to be displayed thereon.

Referring next to the flow charts of FIGS. 3 and 4, there will be described the operation of the blood pressure monitoring system.

Figure 3:
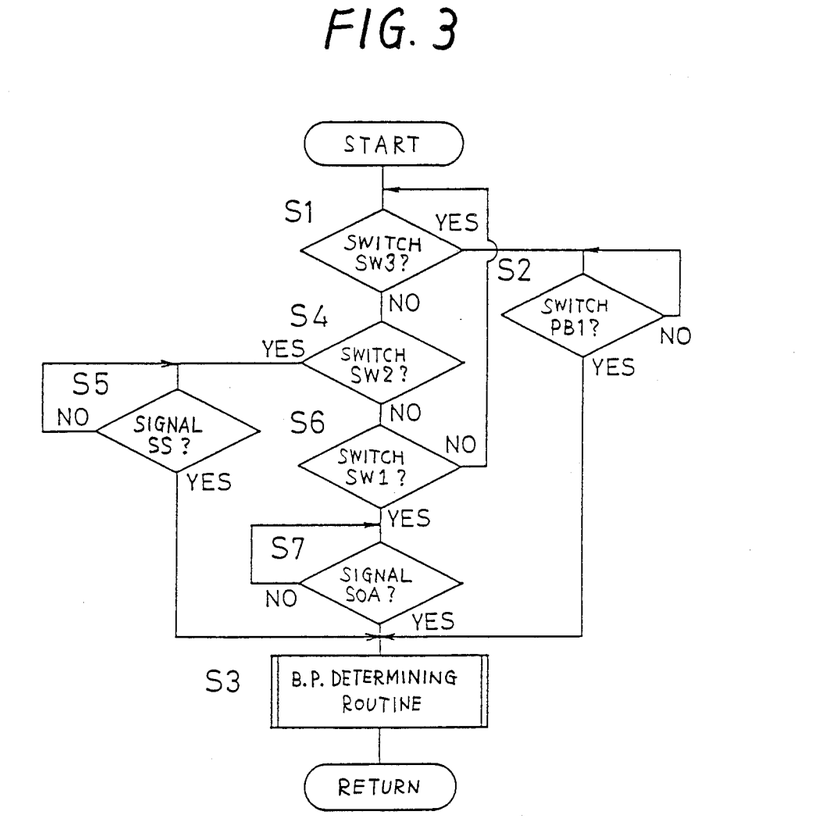
FIGS. 3 and 4 are a view illustrating a flow chart used for operating the monitoring system of FIG. 1, respectively.

Initially, step S1 on the flow chart of FIG. 3 is executed by the CPU 50 to check whether or not the manual-operation switch SW3 has been operated to select the manual operation mode, that is, whether or not signal ST from the switch SW3 is present in the I/O port 30. If the manual-operation mode is selected, that is, if the present monitoring system is in the manual-operation mode, step S1 is followed by step S2 at which it is checked whether or not the starting button PB1 has been depressed, that is, whether or not signal MS from the starting button PB1 is present in the I/O port 30. If signal MS is not present in the I/O port 30, that is, if the checking at step S2 is found "NO", step S2 is repeated until the checking shows "YES". If the checking at step S2 is "YES", that is, indicates that signal MS is present in the I/O port 30, step S2 is followed by step S3. At step S3, a blood-pressure determining routine is executed to determine a measure of blood pressure of the subject. The blood-pressure determining routine includes a plurality of steps, which will be described below in detail.

Figure 4:
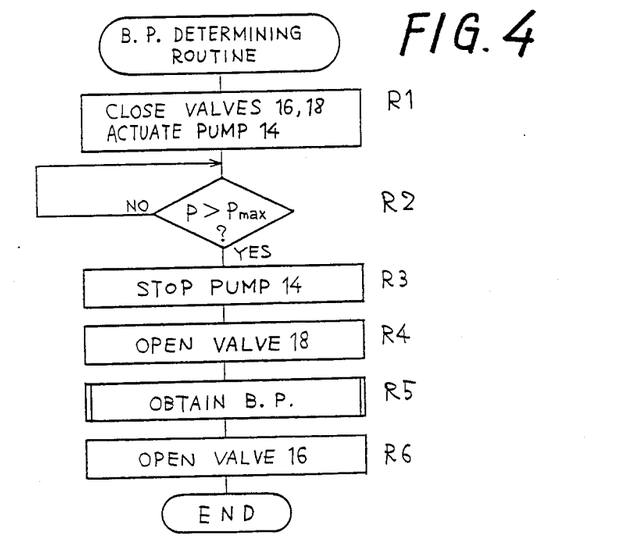

FIG. 4 shows a sequence of steps used for the blood-pressure determining routine. First, step R1 is executed to close the rapid-deflation and slow-deflation selenoid valves 16 and 18 and generate signal PD to actuate the electrically-operated pump 14. Thus, the inflatable cuff 10 would around a part of the subject is inflated, and the part of the subject is oppressed. Subsequently, step R1 is followed by step R2 at which it is checked whether or not a level of pressure P in the inflated cuff 10 which is indicated by signal SPD from the first discriminator 26 has exceeded a predetermined maximum pressure $P_{max}$. If the checking at step R2 is found "NO", that is, if the pressure P in the cuff 10 has not yet exceeded $P_{max}$, step R2 is repeated. In the meantime, if the checking at step R2 becomes "YES", step R3 is executed to stop the electrically-operated pump 14. Consequently, the pressure P in the cuff 10 is held at the increased level above the pressure $P_{max}$. The pressure $P_{max}$ is predetermined above a maximum (systolic) blood pressure of the subject to be monitored.

Step R3 is followed by step R4. At step R4, the CPU 50 generates signal MD2 from the I/O port 30 to the slow-deflation solenoid valve 18 so that the valve 18 is opened. Accordingly, air in the inflated cuff 10 is slowly discharged through the restrictor member 20 and the valve 18, and the pressure P in the cuff 10 is gradually lowered. Subsequently, step R5 is executed to obtain a measure of blood pressure of the subject. At step R5, the maximum and minimum blood pressure is obtained as follows. First, points are determined at which the rate of change in the magnitude of oscillations of the presence in the cuff 10 that are represented by signals SMD supplied from the second discriminator 28, becomes maximal. As previously mentioned, the oscillations of the pressure in the cuff 10 correspond to pulse waves propagated to the cuff 10 through the part of the subject around which the cuff 10 is wound. The thus-determined points are defined as maximum and minimum blood pressure points. And, the values of the pressure in the cuff 10 corresponding to those points are regarded as the maximum and minimum blood pressure. Next, the thus-obtained measure of blood pressure is indicated on the display 56. Step R5 is followed by step R6 at which the CPU 50 generates signal MD1 to the rapid-deflation solenoid valve 16 so that the valve 16 is opened to rapidly discharge air from the inflatable cuff 10, and that the oppression is removed from the part of the subject being monitored. The blood pressure determining routine, i.e., step S3 or steps R1-R6 cooperate with the members 10, 12, 14, 16, 18, 20, 24, 26, 28 and others to constitute the determining means of the present monitoring system.

After the sequence of steps R1-R6 have been executed at step S3 to determine a measure of blood pressure of the subject, the control or CPU 50 returns to step S1.

In the case where the manual-operation mode has not been selected, that is, if the checking at step S1 is found "NO", step S1 is followed by step S4. At step S4, it is checked whether or not the periodical-measuring switch SW2 has been operated, that is, whether or not signal SC is present in the I/O port 30. In the case where the switch SW2 has been operated, that is, if the system is placed in its periodical-measuring mode, step S4 is followed by step S5 at which it is checked whether signal SS periodically supplied from the trigger device 32 is present in the I/O port 30. As previously described, signal SS is utilized by the CPU 50 for starting the determining means so as to obtain a measure of blood pressure. If signal SS is not present in the I/O port 30, step S5 is repeated. Meanwhile, once signal SS is supplied from the trigger device 32 and present in the I/O port 30, the CPU 50 goes to step S3 for obtaining a measure of blood pressure.

It can be said that blood pressure measurement is not necessarily conducted at the time the subject being monitored becomes worse or abnormal with respect to the degree of saturation of oxygen in blood, in the periodical-measuring mode described above.

In the case where the present blood pressure monitoring system is placed in its automatic-operation mode, that is, in the case where the automatic-operation switch SW1 has been operated, the checking at step S4 is found "NO", and the checking at step S6 to check whether or not signal SA is present in the I/O port 30, is found "YES". If the switch SW1 has not been operated, the checking at step S6 is found "NO", and the CPU 50 returns to step S1 so as to execute the following steps. Since the sytem is now in its automatic-operation mode, step S6 is followed by step S7 to check whether or not signal SOA representative of abnormality of the degree of saturation of oxygen in blood of the subject is present in the I/O port 30. If signal SOA is not present in the port 30, step S7 is repeated. In the meantime, if signal SOA is supplied from the oxymeter 34, the CPU 50 goes to step S3 to immediately obtain a measure of blood pressure of the subject and show on the display 56 the figures indicative of the obtained blood pressure.

As is understood from the above description, blood pressure measurement is automatically conducted at the time the subject being monitored is brought into an abnormal blood state, in responding to signal SOA, in the case where the present system is placed in its automatic-operation mode. Thus, the automatic-operation mode is used with much advantage, for example, for the purpose of monitoring a patient during or after a surgical operation. Since a measure of blood oxygen is obtained upon detection of abnormality in the blood of the patient (subject), medical treatment or aid is given to the patient without delay. Further, the present monitoring system provides another advantage in that the inflatable cuff 10 never applies oppression to the subject at the time blood pressure measurements need not be obtained from the subject. Thus, the subject (patient) being monitored does not suffer any unnecessary oppression or congestion.

The instant monitoring system is adapted to detect abnormality of the degree of saturation of oxygen in blood which flows within a peripheral part of the subject, the finger 36, at which change of condition of the circulatory system is initially exhibited. In the case where the present system is used for monitoring a subject who is undergoing an exercise test or activity test, it can find the subject brought into shock immediately and start to obtain a measure of blood pressure of the subject in the shock state.

Figure 5:
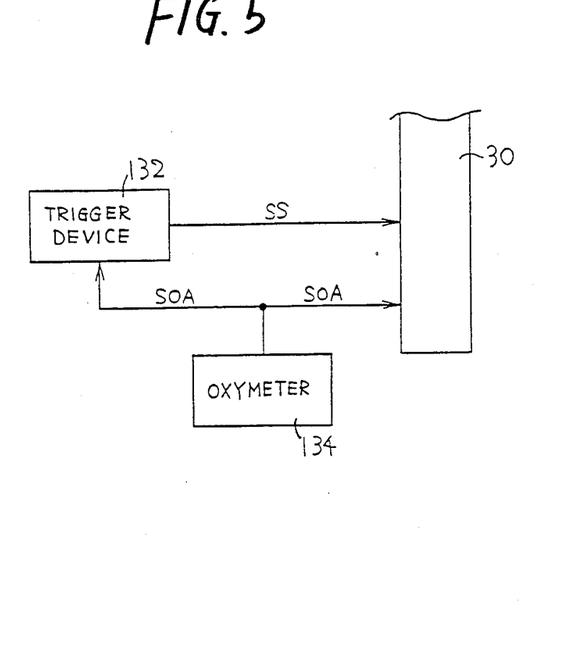
FIG. 5 is a diagrammatical view partially illustrating another embodiment of the monitoring system according to the present invention.

Referring next to FIG. 5, there is illustrated another embodiment of an automatic blood pressure monitoring system according to the present invention.

The present embodiment is similar to the previously-described embodiment, except that an oxymeter 134 generates signal SOA indicative of abnormality of the degree S, not only to I/Oport 30 so as to immediately start the operation for determining a measure of blood presure, but also to a trigger device 132. The trigger device 132 of the present embodiment functions to generate starting signal SS at intervals so as to periodically start the operation for obtaining a measure of blood pressure from the subject, as the trigger device 32 of the previous embodiment does. For example, the device 132 may be adapted to generate starting signal SS every 15 minutes. However, with signal SOA supplied from the oxymeter 134, the trigger device 132 shortens the intervals, that is, generates starting signal SS at shortened intervals. For example, the intervals may be changed from 15 minutes to 1 minute.

In the instant monitoring system, at the time the subject being monitored becomes abnormal with respect to the degree S of saturation of oxygen in the blood, the oxymeter 134 generates signal SOA to both the I/O port 30 and the trigger device 132. In the case where the monitoring system is placed in its periodical-measuring mode, therefore, the system is responsive to signal SOA indicative of abnormality of the degree S, to continuously obtain blood pressure measurements from the subject at shortened intervals. This is very advantageous from the clinical viewpoint.

While the present invention has been described in detail in its preferred embodiments, it is to be understood that the present invention may be embodied with other improvments, modifications and changes.

For example, the oxymeter 34 may be adapted to detect abnormality of the degree of saturation of oxygen of the blood, at an ear of the subject, in place of at the finger 36.

The functions of the calculator element 45, aborrmality discriminator 46 and manually-operable device 47 all of which serve for the oxymeter 34 may be replaced by program which is stored in the ROM 54 or other storing means. In this case, signals V1 and V2 generated by the first and second photosensors 41 and 42 are supplied to the I/O port 30 by way of A/D converter.

While the illustrated embodiments are adapted to determine, at step R5 of Fgi. 4, a measure of blood pressure based on change in the magnitude of pulse waves indicated by signals SMD, the measure may be determined based on the pressure in the cuff 10 at the time Korotkov's sounds appear and disappear to be heard through a microphone. Korotkov's sounds are caused by pulse waves propagated to the part of the subject around which the inflatable cuff 10 is wound, while the inflated cuff 10 is slowly deflatd. Alternatively, the measure of blood pressure may be determined based on variation in the magnitude of pulsory motion of pulse waves propagated on the surface of the wall of an artery in the part of the subject around which the cuff 10 is wound, while the cuff 10 is deflated.

The illustrated embodiments are adapted to determine a measure of blood pressure while the inflated cuff 10 is slowly deflated. However, it is possible to determine the measure while the inflatable cuff 10 is inflated to oppress a part of the subject being monitored.

The first embodiment of the blood pressure monitoring system may be modified to have the automatic-operation mode only. In this case, the swites SW1, SW2, SW3 and PB1 are omitted, and steps S1, S2, S4, S5 and S6 on the flow cart of FIG. 4 are also omitted.

It is noted that the present invention may be embodied with further changes that may occur to those skilled in the art, without departing from the scope and spirit of the present invention defined in the following claims.

What is claimed is:

1. An automatic blood pressure monitoring system for automatically obtaining blood pressure measurements, comprising:

determining means for determining a measure of blood pressure of a living body;

detecting means for detecting a degree of saturation of oxygen in blood which flows in a peripheral part of said living body, said detecting means generating a signal representative of an abnormality if said degree of saturation of oxygen is found abnormal; and control means responsive to said signal supplied from said detecting means, to start said determining means to determine said measure of blood pressure of said living body.

2. An automatic blood pressure monitoring system as recited in claim 1, wherein said detecting means comprises an air bag for oppressing said peripheral part of said living body so as to remove the blood out of veins and arteries of the peripheral part.

3. An automatic blood pressure monitoring system as recited in claim 2, wherein said detecting means further comprises a lamp for emitting light toward said pheripheral part of said living body, said light emitted by said lamp being transmitted through the peripheral part.

4. An automatic blood pressure monitoring system as recited in claim 3, wherein said detecting means further comprises first sensor means for selectively receiving light of a first wavelength range out of said light which has been transmitted through said peripheral part of said living body, the amount of said first wavelength range light received by said first sensor means being varied in association with the volume of blood at said peripheral part and the quantity of tissue at said peripheral part but remaining unaffected by the degree of saturation of oxygen in said blood, said first sensor means generating a first signal corresponding to the amount of the first wavelength range light received, said detecting means also comprising second sensor means for selectively receiving light of a second wavelength range out of the light which has been transmitted through the peripheral part, the amount of said second wavelength range light received by said second sensor means being varied in association with the volume of blood at the preiphral part, the quantity of tissue at the peripheral part and the degree of saturation of oxygen in the blood, said second sensor means generating a second signal corresponding to the amount of the second wavelength range light received.

5. An automatic blood pressure monitoring system as recited in claim 4, wherein said lamp emits said light and said first and second sensor means receive said first and second wavelength range lights and generate said first and second signals, respectively, and means are provided to operate said lamp and said signals in both cases where said peripheral part of said living body is oppressed by said air bag and where the peripheral part is not oppressed by the air bag.

6. An automatic blood pressure monitoring system as recited in claim 5, wherein said detecting means further comprises calculator means for receiving said first signal from said first sensor means and said second signal from said second sensor means, in said both cases, said calculator means determining said degree of saturation of oxygen in the blood of the living body, based on the first and second signals received in the both cases, and generating signal representative of said degree determined.

7. An automatic blood pressure monitoring system as recited in claim 6, wherein said detecting means further comprises storing means for storing a reference degree of saturation of oxygen and generating a signal representative of said reference degree stored, said detecting means also comprising abnormality discriminator means for receiving said signal from said calculator means and said signal from said storing means, checking if said degree determined by said calculator means is abnormal compared to said reference degree stored by said storing means, and generating to said control means a signal representative of an abnormality if the degree determined by the calculator means is found abnormal.

8. An automatic blood pressure monitoring system as recited in claim 4, wherein said first light selectively received by said first sensor means has wavelengths of around 800 millimicrons, while said second light selectively received by said second sensor means has wavelengths of around 600 m$\mu$.

9. An automatic blood pressure monitoring system for automatically obtaining blood pressure measurements, comprising:
   determining means for determining a measure of blood pressure of a living body;
   detecting means for detecting a degree of saturation of oxygen in blood which flows in a peripheral part of said living body, said detecting means generating a signal representative of an abnormality if said degree of saturation of oxygen is found abnormal; and
   trigger means for generating a first signal at intervals to periodically start said determining means so as to determine said measure, said trigger means being responsive to said signal supplied from said detecting means, to generate a second signal at intervals shorter than said intervals at which to generate said first signal, so as to periodically start said determining means for determining said measure.

* * * * *